US00PP33154P3

(12) United States Plant Patent
Mazzardis

(10) Patent No.: US PP33,154 P3
(45) Date of Patent: Jun. 15, 2021

(54) BLUEBERRY PLANT NAMED 'NS 15-5'

(50) Latin Name: ***Vaccinium* hybrid**
Varietal Denomination: NS 15-5

(71) Applicant: Next Progeny Pty., Ltd., Subiaco (AU)

(72) Inventor: Vincent David Andrew Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 17/087,369

(22) Filed: Nov. 2, 2020

(65) Prior Publication Data

US 2021/0144895 P1 May 13, 2021

(30) Foreign Application Priority Data

Nov. 12, 2019 (QZ) ..... PBR 2019/2934

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt
(74) *Attorney, Agent, or Firm* — Randall Danskin, P.S.

(57) ABSTRACT

A new and distinct variety of blueberry plant, which is denominated varietally as 'NS 15-5' is described, with a medium to dense fruit cluster density and which produces fruit considered large to very large in size and very low to low in acidity under the ecological conditions prevailing in Yanchep, Western Australia.

2 Drawing Sheets

Latin name: *Vaccinium* hybrid.
Variety denomination:
The invention relates to a new, novel, and distinct variety of blueberry plant, a *Vaccinium* hybrid, with a variety denomination hereinafter as 'NS 15-5'.

CROSS REFERENCE TO RELATED APPLICATIONS

This application claims the benefit of priority under 35 USC § 119 to Community Plant Variety Office (CPVO) Application No. 2019/2934 for Community Plant Variety Rights, filed on Nov. 12, 2019 for a blueberry plant with a variety denomination of 'NS 15 5', which is herein incorporated by reference in its entirety.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, cross-pollinations were made in order to produce plant populations from which improved progeny were evaluated and thereafter selected.

The 'NS 15-5' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant 'EB 9-4' (U.S. Plant Pat. No. 28,334), and a pollen parent, blueberry plant 'EB 8-46' (U.S. Plant Pat. No. 26,173) during the 2013 growing season.

PRIOR VARIETIES

The seed parent 'EB 9-4' is characterized principally by a semi-upright to intermediate growth habit, a medium vigor, a very early season first pick date, and further produces large- to very-large-sized, firm, high sweetness, and low to medium acidity fruit under the ecological conditions occurring in Yanchep, Western Australia. Also, the seed parent 'EB 9-4' exhibits a very early date of bloom time, a medium fruit cluster density, and a last pick date in February of the following year under the ecological conditions occurring in Yanchep, Western Australia. Further, the seed parent 'EB 9-4' is evergreen and produces fruit on one-year-old and current season's shoots.

The pollen parent 'EB 8-46', on the other hand, is characterized principally by an intermediate growth habit, a medium to strong vigor, an early season first pick date, and further produces very-large-sized, firm to very firm, high sweetness, and low acidity fruit under the ecological conditions occurring in Yanchep, Western Australia. Also, the pollen parent 'EB 8-46' exhibits an early date of bloom time, a medium to dense fruit cluster density, and a November last pick date under the ecological conditions occurring in Yanchep, Western Australia. Further, the pollen parent 'EB 8-46' is semi-evergreen and produces fruit on one-year-old and current season's shoots.

ORIGIN

The seed from the seed parent 'EB 9-4' produced approximately 2,400 plants following cross-pollination. These new plants were then grown at the aforementioned property, and fruit from these new plants was first observed in 2014. A subsequent assessment of these same self-fertile, new plants conducted during the 2015 growing season led to selecting the 'NS 15-5' variety for further evaluation.

ASEXUAL REPRODUCTION

The further evaluation included an asexual vegetative propagation, by vegetative cuttings, at Yanchep Springs in Yanchep, Western Australia. Subsequent evaluations of the newly derived plants in the 2016 growing season led to a conclusion that the 'NS 15-5' variety was a distinct and new variety of blueberry plant found to be true to the original plant. The new variety of blueberry plant was considered to be novel in view of its large to very large fruit size, medium to dense fruit cluster density, and very low to low fruit acidity.

COMPARISONS

In comparison to the seed parent 'EB 9-4' under the ecological conditions occurring in Yanchep, Western Australia, the new variety is noteworthy. In this regard, the seed parent and the new variety of blueberry plant both produce fruit with a size considered to be large to very large. In addition, the seed parent has a fruit cluster density considered to be medium. In contrast, the new variety of blueberry plant has a fruit cluster density considered to be medium to dense. Further, the seed parent produces fruit considered to be low to medium in acidity. This is in contrast to the fruit of the new variety of blueberry plant, which is considered to be very low to low in acidity.

In comparison to the pollen parent 'EB 8-46' under the ecological conditions occurring in Yanchep, Western Australia, the new variety is noteworthy. In this regard, the pollen parent produces fruit with a size considered to be very large. However, the new variety of blueberry plant produces fruit with a size considered to be large to very large. In addition, the pollen parent and the new variety of blueberry plant both have a fruit cluster density considered to be medium to dense. Further, the pollen parent produces fruit considered to be low in acidity. This is in contrast to the fruit of the new variety of blueberry plant, which is considered to be very low to low in acidity.

The new variety of blueberry plant is readily distinguishable from the most closely related, known variety, the 'EB 12-3' blueberry plant described in Australia Plant Breeder Right 2017/316, filed Oct. 31, 2017, titled "Southern Highbush Blueberry (*Vaccinium* hybrid) Variety EB 12-3," which is herein incorporated by reference in its entirety. In this regard, the closest known variety 'EB 12-3' produces fruit with a size considered to be large. However, the new variety of blueberry plant produces fruit with a size considered to be large to very large. In addition, the closest known variety has a fruit cluster density considered to be medium. In contrast, the new variety of blueberry plant has a fruit cluster density considered to be medium to dense. Further, the closest known variety produces fruit considered to be medium to high in acidity. This is in contrast to the fruit of the new variety of blueberry plant, which is considered to be very low to low in acidity. Although 'EB 12-3' produces fruit with medium to high acidity when the fruit turns full blue in ripeness, it should be noted that fruit remaining on the plant for another 7 to 10 days increases in size and decreases in acidity to low to medium acidity.

The comparisons described above are summarized in Table 1 below.

TABLE 1

Summary of Comparisons

| | 'NS 15-5' | 'EB 12-3' | 'EB 9-4' (Seed) | 'EB 8-46' (Pollen) |
|---|---|---|---|---|
| Fruit size | Large to very large | Large | Large to very large | Very large |

TABLE 1-continued

Summary of Comparisons

| | 'NS 15-5' | 'EB 12-3' | 'EB 9-4' (Seed) | 'EB 8-46' (Pollen) |
|---|---|---|---|---|
| Fruit cluster density | Medium to dense | Medium | Medium | Medium to dense |
| Fruit acidity | Very low to low | Medium to high | Low to medium | Low |

In addition, Table 2 below compares the 'NS 15-5' variety to several sibling cultivars that resulted from same the seed parent 'EB 9-4' and pollen parent 'EB 8-46', namely, 'NS 15-13' (U.S. Plant patent application Ser. No. 16/990,818), 'NS 15-22' (U.S. Plant patent application Ser. No. 16/991,651), and 'NS 16-15' (U.S. Plant patent application Ser. No. 16/991,868).

TABLE 2

Comparison to Sibling Cultivars

| | 'NS 15-5' | 'NS 15-13' | 'NS 15-22' | 'NS 16-15' |
|---|---|---|---|---|
| Fruit size | Large to very large | Large | Large to very large | Large |
| Fruit cluster density | Medium to dense | Sparse to medium | Medium | Dense |
| Fruit acidity | Very low to low | Low to medium | Low | Low |
| Fruiting type | on one-yr-old and current season's shoots | on one-yr-old shoots only | on one-yr-old shoots only | on one-yr-old shoots only |
| Vegetative bud burst timing | Early, end of May | Early, end of May | Early, end of May | Early, mid-Jun |
| Fruit sweetness | Medium | Medium | Medium | Medium |
| Fruit firmness | Medium | Medium to firm | Medium | Firm |
| Plant vigor | Strong | Medium to strong | Strong | Medium to strong |

BRIEF DESCRIPTION OF THE DRAWINGS

The accompanying drawings are color photographs of the new blueberry plant 'NS 15-5' during the third year of growth under the ecological conditions prevailing at the breeder's property, which is located at Yanchep Springs in Yanchep, Western Australia.

Figure 1:
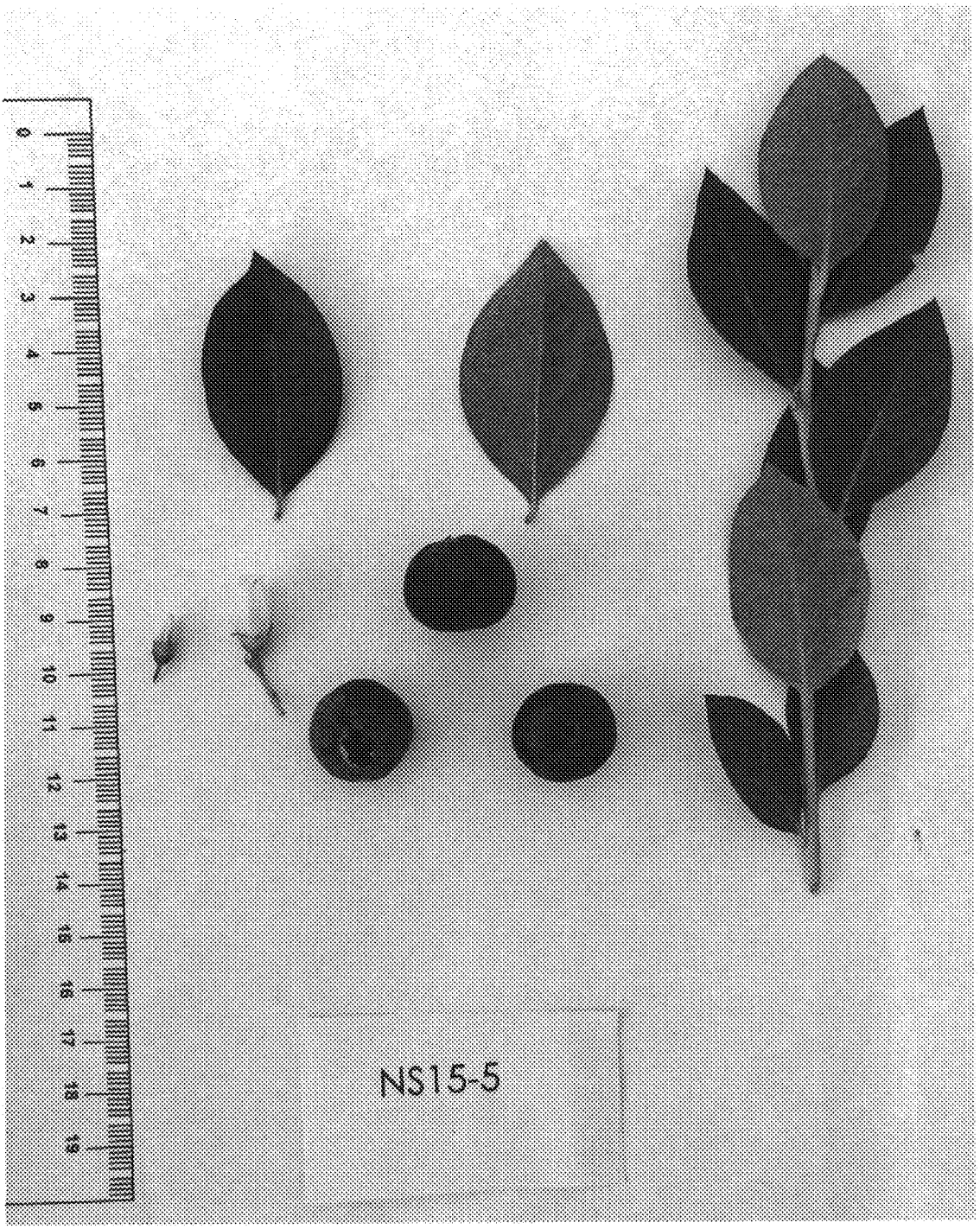
FIG. 1 is a color photograph, which shows fruit, blooms, leaves, and a portion of a vegetative stem of the new blueberry plant 'NS 15-5', the fruit being sufficiently mature for harvesting and shipment. This photograph also depicts the fruit size and the color of the ripe fruit, two leaves showing the sizes and the upper and under side colorations thereof, two blooms at different stages of maturation, and additional leaves on the stem at different stages of maturation.
Figure 2:
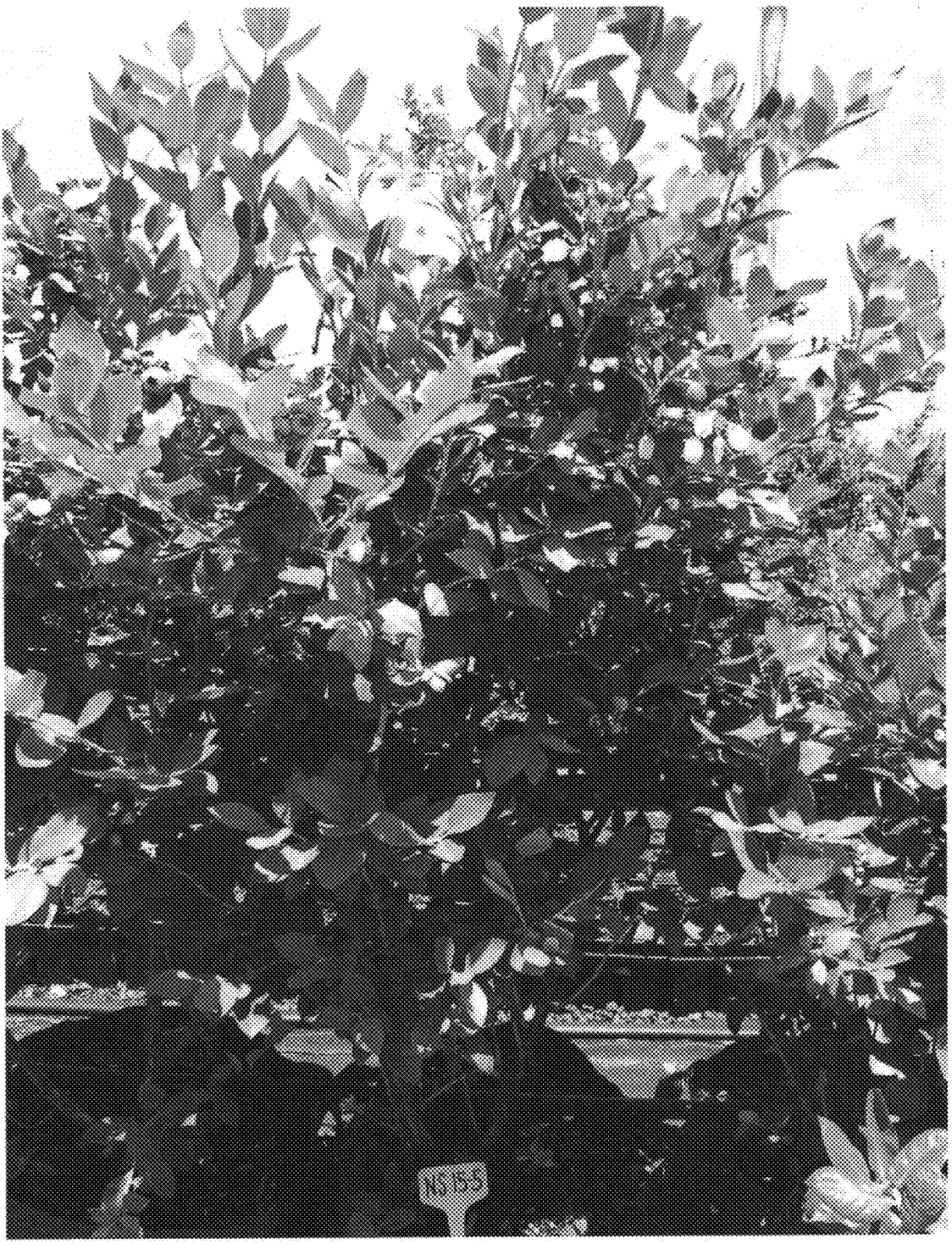
FIG. 2 is a color photograph, which shows the new blueberry plant 'NS 15-5'. This photograph depicts a mature bush with ripe and unripe fruits, the fruit size, and the upright growth habit of the bush. The ripe fruit is sufficiently mature for harvesting and shipment.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition (2015), hereinafter, "R.H.S.") and descriptions provided.

DETAILED BOTANICAL DESCRIPTION

Not a Commercial Warranty

The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the third year of growth under the ecological conditions prevailing at the breeder's property, which is located at Yanchep Springs in Yanchep, Western Australia.

Plant: General.

*Vigor.*—Considered strong for the species.

*Growth habit.*—Considered upright. This is in comparison to the commercial variety 'Ivanhoe' (unpatented), which is considered to be upright.

*Average size of plant.*—1.1 meters in height by 0.90 meters in width.

*Internode length* (*space between nodes*).—Considered short to medium, 12-18 millimeters (mm).

*Bark color.*—RHS Brownish Orange Group 164A.

*Color, one year old shoots.*—RHS Light Yellow Green Group 145B.

*Fruiting type.*—On one-year-old shoots and current season's shoots, in like manner to commercial varieties 'Concord' (unpatented) and 'Burlington' (unpatented).

Foliage: General.

*Average leaf length.*—Considered medium to long for the species, 60.7 mm.

*Average leaf width.*—Considered medium to broad for the species, 30.9 mm.

*Color of leaf upper.*—RHS Deep Yellowish Green Group 144A.

*Color of leaf underside.*—RHS Moderate Yellow Green Group 138B.

*Vein color of plant leaf.*—RHS Strong Yellow Green Group 144B.

*Venation pattern of leaf.*—Pinnate reticulate.

*Leaf apex texture.*—Glabrous.

*Leaf apex shape.*—Acute.

*Leaf base shape.*—Acute.

*Leaf shape.*—Ovate.

*Leaf margin.*—Entire.

*Leaf arrangement of plant.*—Alternate.

*Petiole length.*—3.71 mm.

*Petiole diameter.*—1.42 mm.

*Petiole color.*—RHS Light Yellow Green 145B.

Flowers.

*Number of flowers/inflorescence.*—8-10.

*Length of inflorescence* (*excluding pedicel*).—Considered medium to long, 9.3 mm.

*Corolla shape.*—Urceolate.

*Corolla tube surface texture.*—Ridges are present on the corolla tube.

*Average corolla length.*—12.7 mm.

*Corolla diameter.*—9.6 mm.

*Corolla aperture size.*—6.45 mm.

*Corolla color.*—RHS White Group NN155C.

*Pedicel color.*—RHS Brilliant Yellow Green Group 149B.

*Pedicel length.*—7.54 mm.

*Average calyx diameter.*—Considered small to medium, 3.86 mm.

*Average calyx basin depth.*—Considered medium, 1.6 mm.

*Attitude of sepals.*—Erect.

*Type of sepals.*—Straight.

Reproductive organs.

*Size of pollen anthers.*—5.46 mm.

*Color of pollen anthers.*—RHS Brownish Orange Group 167B.

*Pistil length.*—9.62 mm.

*Pistil color.*—RHS Brilliant Yellow Green Group 149B.

Fruit.

*Color of unripe fruit.*—RHS Strong Yellow Green Group 144A.

*Color of fruit skin.*—RHS Bluish Black Group 203C, also considered "dark blue" in like color to the commercial variety 'Heerma' (unpatented), after removal of bloom.

*Color of ripe fruit flesh.*—RHS Light Yellow Green Group 144D.

*Color of seeds.*—RHS Brownish Orange Group N167B.

*Average fruit size.*—Large to very large, 20 mm in diameter and 13.53 mm in height. This is comparable to the seed parent 'EB 9-4', wherein the fruit size is also considered large to very large. This is in contrast to the pollen parent 'EB 8-46', wherein the fruit size is considered very large. This is also in contrast to the closest known variety 'EB 12-3', wherein the fruit size is considered large.

*Average weight of fruit.*—3.37 grams.

*Berry shape.*—Considered oblate.

*Sweetness when ripe.*—Considered medium for the species.

*Firmness when ripe.*—Considered medium for the species.

*Acidity when ripe.*—Considered very low to low for the species. This is in contrast to the seed parent 'EB 9-4', wherein the fruit acidity is considered low to medium. This is also in contrast to the pollen parent 'EB 8-46', wherein the fruit acidity is considered low. This is further in contrast to the closest known variety 'EB 12-3', wherein the fruit acidity is considered medium to high.

*Cluster density.*—Considered medium to dense for the species. This is comparable to the pollen parent 'EB 8-46', wherein the fruit cluster density is also considered medium to dense. This is in contrast to the seed parent 'EB 9-4' and the closest known variety 'EB 12-3', wherein the fruit cluster density is considered medium.

*Average fruit production.*—3 kilograms on a two-year-old bush.

*Storability of fruit.*—Considered excellent for the species.

*Market use of fruit.*—1st grade fresh market fruit.

*Date of bud burst.*—This variety is evergreen under the ecological conditions prevailing in Yanchep, Western Australia, but a bud break occurs at the end of May, which is considered early for the species.

*Date of bloom time.*—This variety is evergreen under the ecological conditions prevailing in Yanchep, Western Australia, but a bloom time occurs in mid-July, which is considered very early on one-year-old shoot in like manner to the commercial variety 'Patriot' (unpatented) and is considered very early on current year's shoot before the commercial variety 'O'Neal' (unpatented), which is considered early.

*Duration of bloom time.*—4 weeks.

*Beginning of fruit ripening.*—considered very early on one-year-old shoot in like manner to the commercial variety 'Bluetta' (unpatented) and very early on current year's shoot before the commercial variety 'O'Neal' (unpatented), which is considered early.

*First pick date.*—The observed date of the first pick is approximately September under the ecological conditions prevailing in Yanchep, Western Australia.

*Last pick date.*—The observed date of the last pick is approximately October under the ecological conditions prevailing in Yanchep, Western Australia.

*Pollination requirements.*—Self-fertile.

*Resistance to pests and disease.*—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a plant letters patent is:

1. A new and distinct variety of blueberry plant named 'NS 15-5,' substantially as illustrated and described, which is characterized principally as to novelty by a medium to dense fruit cluster density and by producing fruit considered large to very large in size and very low to low in acidity under the ecological conditions prevailing in Yanchep, Western Australia.

* * * * *